United States Patent [19]

Hottinger

[11] 4,381,787

[45] May 3, 1983

[54] ULTRASOUND IMAGING SYSTEM COMBINING STATIC B-SCAN AND REAL-TIME SECTOR SCANNING CAPABILITY

[75] Inventor: Charles F. Hottinger, Englewood, Colo.

[73] Assignee: Technicare Corporation, Solon, Ohio

[21] Appl. No.: 178,487

[22] Filed: Aug. 15, 1980

[51] Int. Cl.³ .............................................. A61B 10/00
[52] U.S. Cl. .................................... 128/660; 73/620
[58] Field of Search .............................. 128/660–663; 73/618–626

[56] References Cited

U.S. PATENT DOCUMENTS

| | | | |
|---|---|---|---|
| 3,251,219 | 5/1966 | Hertz et al. | 73/642 |
| 3,451,260 | 6/1969 | Thurstone | 73/614 |
| 3,470,868 | 10/1969 | Krause et al. | 128/660 |
| 3,765,228 | 10/1973 | Halsey | 73/599 |
| 3,854,471 | 12/1974 | Wild | 128/660 |
| 3,992,925 | 11/1976 | Perilhou | 73/624 |
| 4,030,344 | 6/1977 | Northeved et al. | 128/660 X |
| 4,037,465 | 7/1977 | Cook et al. | 125/9 |
| 4,058,001 | 11/1977 | Waxman | 128/660 |
| 4,058,114 | 11/1977 | Soldner | 172/363 |
| 4,061,415 | 12/1977 | Taenzer | 350/6.3 |
| 4,063,549 | 12/1977 | Beretsky et al. | 128/660 |
| 4,084,582 | 4/1978 | Nigam | 128/660 |
| 4,110,723 | 8/1978 | Hetz et al. | 367/67 |
| 4,128,012 | 12/1978 | Soldner | 73/611 |
| 4,131,023 | 12/1978 | Mezrich et al. | 73/606 |
| 4,131,024 | 12/1978 | Mezrich et al. | 73/606 |
| 4,131,025 | 12/1978 | Mezrich et al. | 73/606 |
| 4,137,777 | 2/1979 | Haverl et al. | 73/620 |
| 4,143,544 | 3/1979 | Nagy et al. | 73/104 |
| 4,151,834 | 5/1979 | Sato et al. | 128/660 |
| 4,168,628 | 9/1979 | Vilkomerson | 73/607 |
| 4,177,679 | 12/1979 | Soldner | 73/625 |
| 4,274,421 | 6/1981 | Dory | 128/660 |
| 4,275,597 | 6/1981 | Quedens et al. | 128/660 X |

Primary Examiner—Kyle L. Howell
Assistant Examiner—Francis J. Jaworski
Attorney, Agent, or Firm—Nancy A. Bird; Audley A. Ciamporcero, Jr.

[57] ABSTRACT

A standard articulated B-scan arm provides positional and directional information for a transducer at its end, based on relative angular displacements of the separate arm segments. A real time scanner, preferably one having a fixed transducer and a fixed oscillating mirror, is freely attachable or detachable from the scan arm. The probe itself is operable either in a real time sector scan or in a static B-scan mode.

12 Claims, 7 Drawing Figures

ULTRASOUND IMAGING SYSTEM COMBINING STATIC B-SCAN AND REAL-TIME SECTOR SCANNING CAPABILITY

FIELD OF THE INVENTION

This invention relates to ultrasound imaging systems, and more particularly to the classes of such systems which employ multiple segment, articulated arms for achieving positional information, and those which utilize self-contained scanning mechanisms for achieving a real-time scan.

BACKGROUND OF THE INVENTION

One well-known type of ultrasound imaging system, which is available commercially from numerous sources including the assignee hereof, is the static B-scan system. These typically involve a multiple segment (e.g. three) articulated arm, with a transducer attached at the end. The angular positions of the respective segments are m and encoded, typically by potentiometer means at the respective joints, whereby there is always available precise positional information concerning the transducer, and hence the portion of the patient being examined. Through mechanical manipulation of the transducer, images of high line density over a large field of view can be generated. Typically, these static images provide hard copy records of the highest image quality available in the ultrasound modality. Static scanning systems also involve disadvantages, however, arising partly from the limiting and cumbersome nature of the articulated arm. That is, the arm often hampers scanning in difficult apertures of the body, and complicates the initial surveying process to locate small lesions or to follow vascular structures. Additionally, the static nature of this display prevents the monitoring of organs in motion, due to respiration, heart action, or the like.

Another class of commercially available imaging system is the real-time variety, typically a sector or a near rectangular segment of a sector. These systems typically utilize small hand-held probes, which allow the user to survey the anatomy, and to follow vascular structures and to observe organs in motion. These systems often involve disadvantages as well, however, chiefly due to the limited field of view, the low line density in the image, and the lack of positional information repeatably to coordinate the viewing of an image with some fixed datum position. These advantages aggregate when there is a need to obtain a high quality hard copy record of the examination, in that the image quality itself often is a limitation, and in any event there is little or no positional information available to determine the precise location from which the hard copy record was obtained.

Recently, systems have been introduced which include dual functions, employing a real-time sector scanning aspect, as well as a static B-scan probe. One such system has been marketed since approximately November 1979 by Rohe Scientific Corporation of Santa Ana, California under the trade designation Model 7000 Static B-Scanning System. The Rohe system employs two discrete and distinct probes, one for conducting a real-time sector scan and the other for a static B-scan. Preferred techniques for use entail utilization of the real-time sector scanning unit for surveying and coarse examination purposes, followed by use of the static B-scan for detailed evaluation and hard copy production with respect to any lesions or the like first located utilizing the hand-held sector probe. The Rohe system therefore entails most of the disadvantages attendant to utilization of separate sector scan and B-scan systems. First, utilization of the sector-scan image for hard copy is somewhat deficient with respect to image quality, and perhaps more seriously lacks positional information which indicates precisely the plane on which the image was observed. Secondly, assuming that the static B-scan aspect is to be utilized for detailed examination and recording of a hard copy, it may well be difficult to relocate a lesion first encountered utilizing the sector scan head; in any event, extensive readjustment of transducer dependent controls is required prior to shifting from one mode to the other. That is, it will be apparent that utilization of transducers of separate, distinct character for static B-scan and real-time sector scan applications, require different functional and signal processing constraints throughout the imaging system, with respect to timing, level selection, and the like.

It is a primary object of the present invention to provide an ultrasound imaging system which combines the beneficial attributes of static B-scan and real-time sector scan systems, by combining those functions in a manner which substantially eliminates their respective disadvantages.

It is a related object to provide a combined static B-scan and real-time sector scan system, utilizing a single transducer mechanism for both functions, whereby the user is free to shift operation back and forth between the respective modes, thereby vastly to increase the utility of the system. It is an associated object that such shifting back and forth may be accomplished free of the need for extensive readjustment or recalibration.

It is yet another object of the principles of the present invention to provide a combined system whereby positional information is available even when images are being developed, and, as desired, recorded, utilizing the real-time scan mode.

In a concurrently filed copending application of C. Hottinger entitled "ULTRASONIC IMAGING SYSTEM EMPLOYING REAL-TIME MECHANICAL SECTOR SCANNER", U.S. Ser. No. 178,482, which is assigned to the assignee hereof, there is disclosed and claimed a class of real-time sector scanners particularly useful in accordance with the principles of the present invention. The Hottinger system sets forth a form of real-time mechanical sector scanner wherein a positionally fixed, focusing transducer emits and receives ultrasound energy along an axis, and an oppositely facing sonic reflector or mirror is pivoted about a fulcrum on the axis, to reflect sonic energy between the transducer and the subject. Thus, beams between the reflection face and the subject lie in a different spatial plane than do beams between the transducer and the subject. In addition to setting forth the basic premise of such operation, the Hottinger application discloses respective embodiments wherein the mirror is located intermediate the transducer and the source of oscillatory motive power, and wherein the mirror is located "outboard" of the transducer relative to the source of oscillatory motive power.

Another concurrently filed, copending application assigned to the assignee hereof, of J. Sorwick entitled "MECHANICAL SECTOR SCANNER HEAD AND POWER TRAIN", U.S. Ser. No. 178,488, sets forth a preferred design for sector scanning heads employing the rationale set forth in the Hottinger application. In accordance with the teachings of the Sorwick application, a preferred arrangement locates the transducer on the side of the oscillating mirror opposite the source of oscillatory power. A curved faced, disc-shaped transducer and an oppositely facing, circular angularly disposed mirror form the transmission and reception path of a mechanical sector scan imaging system. The transducer and mirror are mounted on a common axis, where the fulcrum for mirror movement also is located. A shaft upon which the mirror is affixed oscillates about the same axis, and through a belt drive mechanism, a spacially eccentric motor provides the oscillating motion to the mirror, in turn scanning ultrasound beams through the subject by virtue of mirror motion. Hence, the Sorwick application describes a configuration which is extremely compact and convenient to use for real-time scanning applications, allowing the user readily to follow patterns of vascularization, to image body portions which are in motion due to respiratory, cardiac, or the like movements, and to have access to difficult to reach portions of the body.

It is an object of the present invention to utilize real-time sector scan apparatus and principles, as taught by the previously referenced Hottinger and Sorwick concurrently filed applications, in conjunction with static B-scan arms and systems, to achieve an efficient, mutually compatible combined system which meets the foregoing objects of the present invention.

SUMMARY OF THE INVENTION

The principles of the present invention are premised on beneficial utilization of a real time sector scanner, for example one such as described and claimed in the aforementioned Hottinger and Sorwick applications, in conjunction with a more traditional static B-scan segmented arm apparatus.

In particular, the sector scan head is detachably mounted at the end of a multiple segment B-scan arm, and depending on whether the rotatable mirror is utilized in an oscillatory or stationary mode, either real time sector, or B-scan modalities may be employed while utilizing a single transducer means. Moreover, both the sector scan and the B-scan approaches may be respectively employed either with the scan head attached to the segmented arm (and hence precisely positionally located as well), or freely movable in the hand of the user (and hence not precisely positionally located).

In a preferred embodiment, a real time sector scanning probe pursuant to the Sorwick application (i.e. with the transducer at an outboard end, and the motor and encoder in a "handle" which is eccentric from the transducer-mirror scan head portion), is freely attachable to and removable from a bracket located at the outermost extremity of a triple jointed B-scan arm. The mirror within the scan head is operable either in an oscillatory (i.e. scanning) mode, or a stationary (i.e. B-scan) mode. Positional information is derived from each joint of the scan arm, and additionally from the position of the mirror itself, whether in motion or fixed in a B-scan position. Pulse-echo information to and from the transducer thereby is spatially coordinated for assembly of a composite image.

In a preferred mode of utilization of the present invention, the scanning probe is first detached from the B-scan arm, and thus hand-held and freely movable as the mirror therein oscillates back and forth through a predetermined sector, produces real time sector scan image for display. In this mode, lesions and areas of interest are easly located. Next, the probe is attached to the articulated B-scan arm while real time imaging again is performed; during this stage, positional information is derived from the joints of the articulated scan arm. This positional information advantageously is displayed along with the image, and, as desired, the superimposed positional information and real time sector image may be recorded. In such fashion, the lesions or other areas of interest are quite accurately and repeatably positionally fixed. Finally, automatic sweeping of the beam (i.e. the mirror) is halted, and the probe and articulated arm are utilized as a conventional B-scan apparatus, advantageously utilizing the identically same transducer, image scale and intensity factors, and the like parameters as were used during the real time procedure. A static image is thereby generated having wide field of view and high line density.

It will be appreciated that the principles of the present invention facilitate ease and coordinated application of real time and static B-scan imaging techniques, substantially maintaining and adopting the superior aspects of each respective system, but for the most part avoiding their respective disadvantages. In particular, a single transducer system is used for both approaches, and the transition is made from sector scan to B-scan without probe changing or extensive readjustment of controls. Additionally, positional information and hence useful hard copy production, is available during the intermediate real time imaging sequences.

BEST MODE FOR CARRYING OUT THE INVENTION

Figure 1:
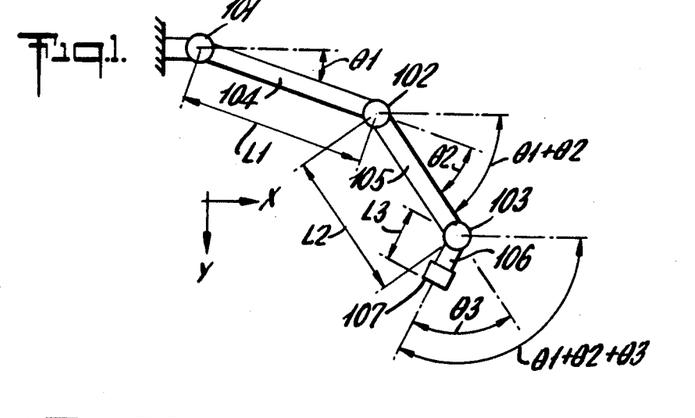
FIG. 1 shows a triple jointed static B-scan arm, and the respective angular components used for positional location in B-scan systems.

Referring first to FIG. 1, there is shown symbolically a multisegmented B-scan arm of a type well known in the art. The arm of FIG. 1 includes three segments 104, 105 and 106, coupled to a fixed reference (not shown in detail) at a top joint 101, and coupled to one another at joints 102 and 103. A bracket 107, shown symbolically in FIG. 1, holds a transducer, which in turn engages the patient in a pulse-echo exchange of sonic energy. The articulated arm of FIG. 1 has means (typically potentiometer circuits) located at each joint 101, 102, and 103 for determining the respective angles $\theta 1$, 174 2, and $\theta 3$. Voltages from the potentiometers thus correspond to the positions of arms 104, 105, and 106 with respect to each other, thereby conclusively identifying the position and orientation of the outermost terminus 107, for example with respect to the positionally stationary joint 101. It will be appreciated from the principles of trigonometry that the location of terminus 107 relative to joint 101 may be resolved into an x and y component, the x component or position being a function of the lengths L1, L2 and L3 of the arms 104, 105, and 106, respectively, and the cosines of the angles $\theta_1$, $(\theta_1+\theta_2)$, and $(\theta_1+\theta_2+\theta_3)$. Likewise, the y component or location of point 107 relative to point 101 will be similarly obtained as a function of the sines of the various angles. Mathematically, the locations of the x and y positional components of point 107 components, are stated as follows:

$P(x) = L1 \cos \theta_1 + L2 \cos (\theta_1+\theta_2) + L3 \cos (\theta_1+\theta_2+\theta_3)$ $P(y) = L1 \sin \theta_1 + L2 \sin (\theta_1+\theta_2) + L3 \sin (\theta_1+\theta_2+\theta_3)$ It will also be apparent that the slope or direction of an ultrasound beam from the transducer at point 107, may be determined based upon the angle $(\theta_1+\theta_2+\theta_3)$, the x slope being a function of the cosine of that angle, and the y slope being a function of the sine of that angle.

Figure 2A:
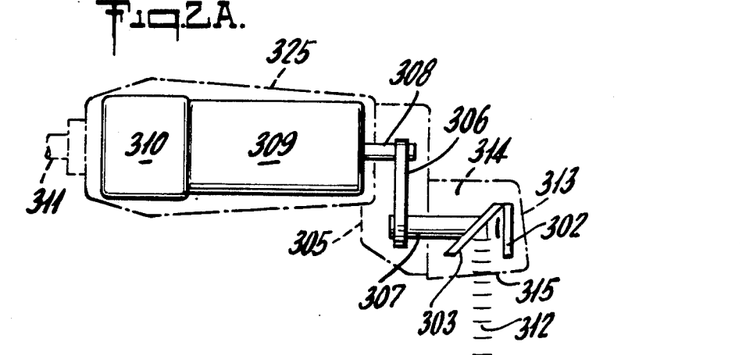
FIGS. 2A and 2B show views of a sector scan head preferably utilized in accordance with the principles of the present invention.
Figure 2B:
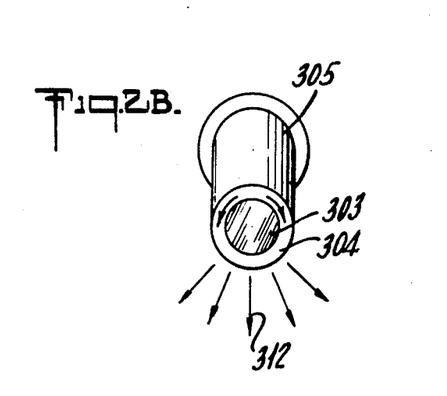

Referring next to FIGS. 2A and 2B, there is shown a preferred scan mechanism for use in accordance with the principles of the present invention. The scan head of FIGS. 2A and 2B embodies the generals precepts set forth in the concurrently filed Hottinger application, and the particular design configuration as set forth in the concurrently filed Sorwick application. In the figures, the transducer 302 is positionally fixed within a lower portion 313 of the head, which forms a fluid chamber 314 and which carries therein a movable mirror 303. Mirror 303 is carried on a shaft 307, which is interconnected with a laterally displaced shaft 308 by means of a drive belt 306. A motor 309 either oscillates shaft 308 back and forth, or rotates it, as preferred, and correspondingly brings about similar movement of the mirror 303. For utilization in a static B-scan mode, the mirror 303 may also be "locked" in place by exerting similar control of the motor 309. In a preferred embodiment, the mirror 303 is to be "locked" in a central position for generation of a single, directly downwardly extending ultrasound beam.

In the real time imaging mode, as the mirror 303 is oscillated or "wobbled", the transducer 302 is fired at a frequency which is substantially faster than the mirror 303 oscillation rate, whereby the emission of a sonic pulse, and reception of an echo series, occurs as an event at substantially a single position for the mirror 303. In other words, the echo signal train returning the transducer 302, as well as the initial firing pulse which created it, occurs substantially instantaneously compared to the rate of motion of the mirror 303. As noted in FIG. 3A, the aggregate of these separate events, resulting from motion of the mirror 303 through a predetermined sector, is the assembly of a sector shaped image from the rotational plane in the body.

Since the mirror 303 moves under power of the motor 309, it will be appreciated that the motion of the mirror 303 needs to be coordinated with the operation of the transducer 302, i.e., with the transmission of sonic energy into the body and receipt of echoes from the body. Accordingly, an encoder 310 is shown next adjacent the motor 309, which encoder 310 serves the function of encoding the angular position of motor 309, and in turn the angular position of mirror 303. Such positional information is important for production of a real time image display, by interrelating signals to and from the transducer, with respect to one another.

It will be appreciated that numerous commercially available and well-known motor and encoder schemes will be suitable for utilization in accordance with the principles of the present invention. For example, the motor 309 is properly embodied either as a continuous (e.g. three phase) motor, or as a stepping or incremental motor. Likewise, the encoder 310 is embodied by a number of alternative schemes, including a magnetic or Hall effect switch, or a continuous optical wheel type encoder which is suitable for direct mounting on a shaft from motor 309.

Figure 3A:
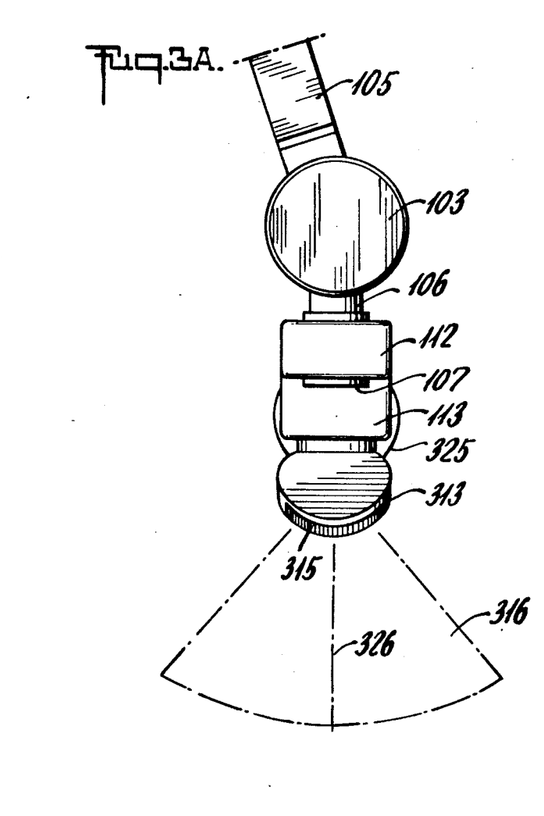
FIGS. 3A and 3B show respective head-on and profile views of a preferred embodiment of the principles of the present invention, with a sector scan head attached at the end of a B-scan arm.
Figure 3B:
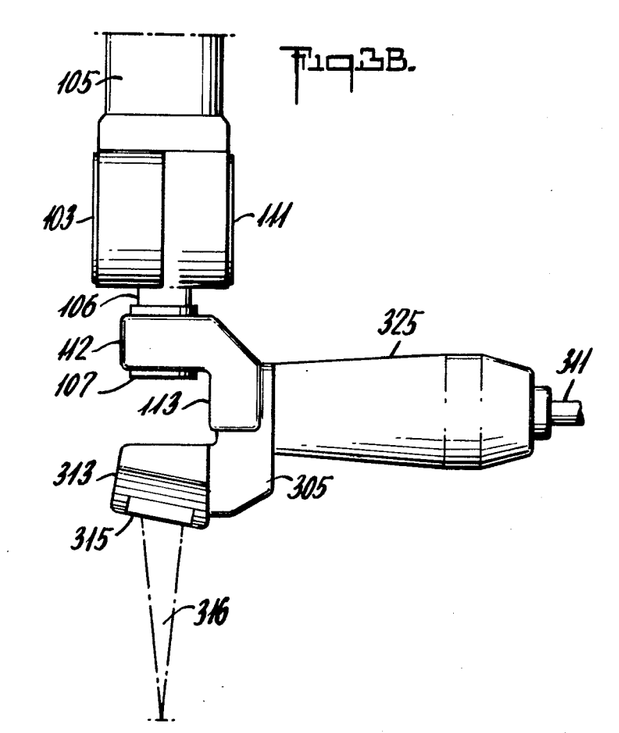

It is to be noted that the physical configuration of the scan head of FIGS. 2A and 2B is well-suited for utilization in accordance with the principles of the present invention. That is, the upper segment 325, enclosing the motor 309 and the encoder 310, is of a convenient size and shape to be grasped in one hand of the ultrasonographer, and useful for a free-hand sort of real time scanning. During such scanning, the lowermost face 315 of the lower portion 313 of the scan head, is in physical contact with the body of the patient, and hence is the point of exit of sonic energy from the scan head, and also is the point of entry of echo signals from the body of the patient. Likewise, the intermediate portion 305, which houses the belt drive mechanism 306 between motor 309 and mirror 303 via shafts 307 and 308, is quite a convenient portion for attachment to a B-scan arm. FIGS. 3A and 3B show a preferred form of bracket, and associated attachment scheme, whereby the sort of scan head shown in FIGS. 2A and 2B, may be utilized at the end point 107 of a segmented scan arm such as shown in FIG. 1.

Prior to consideration of FIGS. 3A and 3B, however, it is appropriate to note that the principles of the present invention are not limited merely to utilization of a configuration shown in FIGS. 2A and 2B. Indeed, broader aspects of the principles of the present invention are not to be limited to the sort of real time scan heads set forth in the previously described Hottinger and Sorwick applications. Instead, it is contemplated that the principles of the present invention will be well-served by utilization of any real time imaging scan head which may be conveniently attached at the end of a scan arm, and which employ transducer schemes suitable both for scanning and static applications. Not the least of these are a number of linear and annular array transducer systems, some of which utilize mirrors and/or lenses to achieve the requisite scanning effect, and others of which utilize compound electronic pulsing techniques to achieve beam steering and shaping.

Referring, then, to FIGS. 3A and 3B, there is shown a preferred embodiment of the principles of the present invention, wherein a mechanical sector scanner such as disclosed and claimed by Sorwick is mounted at the end of a multisegment B-scan arm. In particular, intermediate segment 105 is shown joined with terminating segment 106 at a joint 103 and 111, in conventional fashion. End portion 107 of segment 106 carries a cantilevered bracket 112, which at sleeve portion 113 engages the intermediate segment 305 of the mechanical sector scan head. It will be noted that, with cantilevered section 112 engaging intermediate section 305, the lower, outermost section 313 of the scan head is located with ultrasonically transmissive window 315 immediately below and in substantial alignment with the end segment 106 of the B-scan arm. Hence, as shown in FIG. 3A in frontal view, and 3B in cross-section, as the scan head is operating in a real time sector scan mode, the field of imaging is as shown in phantom at 316. When the scan head has its mirror "locked" for more conventional B-scan operation, pulse transmission and echo receipt occurs on the center line 326 of the sector image field 316 and in direct alignment with segment 106.

As is also noted from FIGS. 3A and 3B, upper section 325 of the scan head extends outwardly from the scan arm—bracket connection, and from the lower, scanning portion 313 and 315, thereby to furnish a convenient handle for manipulation of the scanning aspects and in turn of the B-scan arm. A cable 311 is connected into the system imaging electronics, for purposes of image production and display, with the ultrasound transmission and echo data, which also is coupled to the system electronics via cable 311. Positional data from the respective joints of the segmented B-scan arm are conveyed separately to the imaging electronics, in conventional fashion, through the arm itself. Thus, the scan head 305, 313, and 325 may as desired be detached from the engaging portion 113 of bracket 112, and be utilized "free-hand" for conduct of scanning investigations.

Figure 4:
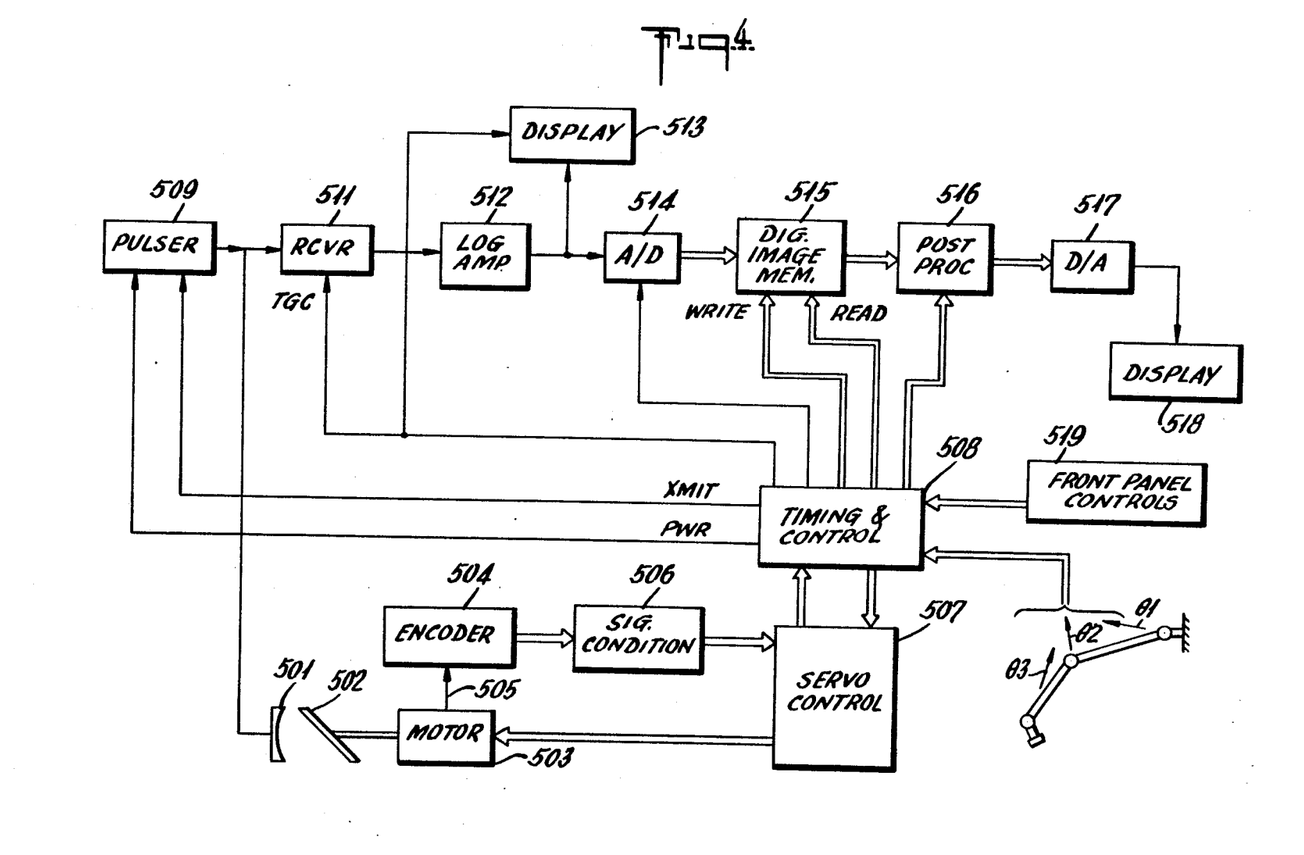
FIGS. 4 and 5 show in block diagrammatic form a diagnostic ultrasound imaging system for producing and presenting images in accordance with the principles of the present invention.
Figure 5:
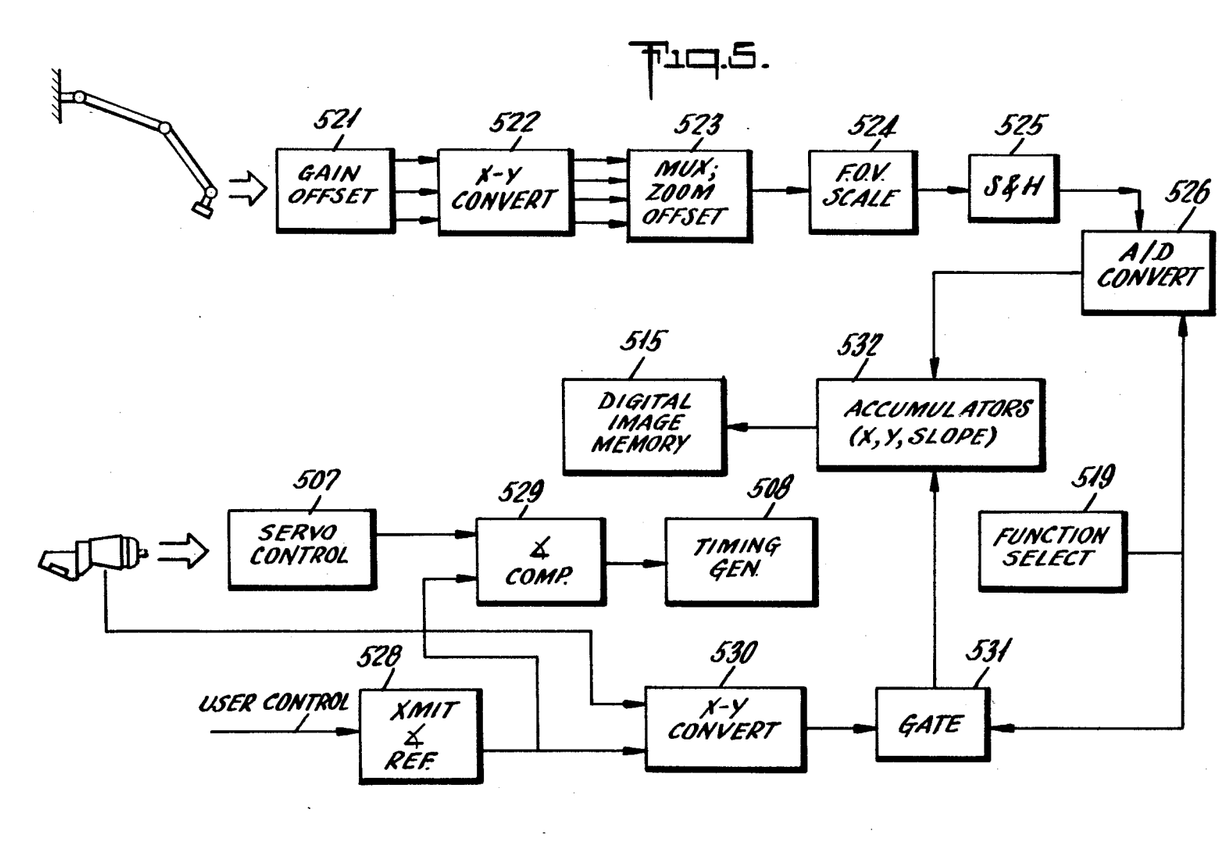

Referring next to FIGS. 4 and 5, there is set forth in block diagrammatic form a signal processing network for a diagnostic imaging system suitable for applications in the principles of the present invention. In particular, FIG. 4 shows an overall block diagram for processing signal bearing information as well as corresponding positional information, and FIG. 5 shows in somewhat greater detail aspects of the timing and control which relate to coordination of those functions, and especially with respect to the positional aspects thereof.

In FIG. 4, the mechanical sector scanner is shown symbolically by means of a fixed transducer 501 facing a rotatable mirror 502. The mirror is located on a shaft drive from the motor 503, which receives energizing control from a servomechanism reference and feedback control 507. An encoder 504, shown being eccentric to the motor shaft 503, but in a preferred embodiment actually being mounted on that shaft, denotes at all times the position of the mirror by denoting the position of the motor shaft 503. The encoded positional information is coupled to signal conditioning circuitry 506, in order to provide suitably scaled information to the servo control 507. Hence, there is presented a closed servomechanism loop between control 507 and mirror 502 whereby the motor oscillation speed is maintained at a desired rate within predetermined tolerance limitations. It will also be clear that the servo control 507, when suitably energized, forces the motor 503 to assume an intermediate "rest" or "locked" position, thereby also affixing mirror 502 in a single position for the B-scan mode.

Information with respect to the angular position of mirror 502 is coupled from the servo reference and feedback control 507 to a timing and control means. Additionally, the three reference angles from the segments of the scan arm are coupled to the timing and control means 508. As also shown in the drawing, control signals from the front panel controls 519 are also coupled to the timing control unit. In conventional fashion, the front panel controls, at the discretion of the user, select frame rate, interlace or noninterlace options, overall sector angle, and the like parameters which dictate the size, granularity, and overall presentation of the sector being imaged. Based on these parameters as selected by the user, the timing and control circuit 508 energizes pulser 509 to deliver electrical signals to fire the transducer 501. As previously described, the sonic energy pulses from transducer 501 are deflected by mirror 502 into the subject. In turn, echoes from the subject are reflected from mirror 502 back to the transducer 501. The impinging of these echoes on transducer 501 is detected by a receiver 511.

The receiver receives a "TGC" control signal from the timing and control module 508. TGC, or time gain compensation, is a standard form of correction, arising because the amplitude of the received pulses decrease exponentially as a function of the depth of tissue from which the echoes have come. Hence there is a need for compensation or equalization to increase the amplitude of echoes in a given train as a function of elapsed time, thereby accounting for the loss which actually occurs.

The corrected signals from the receiver 511 are coupled to a logarithmic amplifier 512, and thence to an analog to digital converter 514. The amplifier 512 compresses the signal into a range which is appropriate for the gray scale being employed by the system. One method of display, known as the "A mode", involves direct coupling of these signals to the display 513. Typically also, such display mode involves a simultaneous display of the TGC signal.

The analog to digital converter 514 accomplishes suitable A to D conversion, typically utilizing a 5 or 6 bit code (depending upon the gray scale being employed), and couples these words preferably in a bit parallel fashion, to a memory 515. In essence, the digital image memory 515 stores a composite image by appropriately locating the actual data from converter 514 in correspondence to the part of the body of the subject which is being displayed. Hence, the digital image memory 515 receives coordination and control from the timing and control unit, whereby each word from converter 514 is conveyed to the proper location in the memory 515. As noted hereinbefore, the servo control loop and the segmented B-scan arm yield encoded information representing appropriate positional information. Therefore, this information may be utilized to place a digital word from A/D converter 514 in a position in correspondence direction and/or position of a beam directed from the mirror 502 into the subject. Likewise, the position and/or direction of each individual word along that beam will be a function of the timing of the received pulse at 511, with respect to its generation from the transducer 501. Such timing is conducted on an ongoing basis at module 508. Hence, the digital image memory appropriately addresses and stores each word from the coder 504.

The digital information in the memory 515, is coupled for display to and through a postprocessing unit 516, thence to a digital to analog converter 517, and to a display 518. The postprocessing function at 516, under control of program selection controls, enables allocation and variation of gray scales in accordance with predetermined transfer curves, in a fashion known in the art. Such operation may utilize, as desired, a large variety of echo amplitude level versus display brightness level allocations, in order to enhance and/or suppress certain desired echoes, or in order to emphasize or de-emphasize particular aspects of the display.

Referring next to FIG. 5, there is shown further detail with respect to some of the timing and control functions of the system of FIG. 4. Considering first the scan arm, angular positional information from the respective joints is coupled to gain and offset amplifier 521, thereby appropriately scaling the voltages representing the respective angles from the scan arm. Next, these three angular voltage quantities are coupled to an x-y converter, which utilizes the previously disclosed trigonometric relationships to convert the three angular quantities, $\theta_1$, $\theta_2$, and $\theta_3$, to x and y positional and directional information at the terminus of the multisegmented scan arm. Thus, four separate values, including x and y position, and x and y direction, are coupled to analog processing circuitry 523. In essence, the unit 523 is an analog multiplexer, which converts the four parallel quantities into a serial format, and as appropriate provides offsets to scale the quantities in accordance with optional "zoom" factors. Next, serialized analog data from the multiplexer 523 is coupled to an analog multiplier 524, where field of view scaling data is combined with the x and y slope and x and y position values. The data from the scaler 524, still in analog form, is coupled to a sample and hold unit 525, and thereupon are applied to an analog to digital converter 526 which reads each applied voltage from the sample and hold unit 525, and produces digital words representing the instantaneous x position, y position, x slope, and y slope values. These position values represent the position of the transducer face (i.e. the contact point with the body of the patient) when the scan head is coupled to the B-scan arm, as shown in FIGS. 3A and 3B.

When the user selects a scan mode which utilizes positional information based on the connection of the scan head to the B-scan arm, as indicated by the function select block 519, the scan arm positional information is coupled from the converter 526 to appropriate accumulators 532. In turn, the information is utilized to guide pulse echo data into the digital image memory 515, as described hereinbefore.

When real time scanning information is to be utilized, either alone or in conjunction with the scan arm positional information, it is necessary to know of the position of the mirror, either in place in a central location, or as it oscillates back and forth through a predetermined sector, and to coordinate this operation with the generation and receipt of sonic energy. Accordingly, the mirror angular position information is coupled from servo control 507 to one input of an angle comparator 529. The other input of angle comparator 529 receives data from a transmit angle reference memory 528, which in turn is controlled as a function of the user controls via function selection block 519.

The significance and operation of the reference memory 528 may be appreciated as follows. Sector scan timing for the embodiments disclosed differs from that for other modes in that transmissions are designed to occur when the mirror reaches certain angles, rather than at set time intervals. In turn, the spacing and location of these angles through a sector are variables to be chosen in accordance with the needs and desires of the user. Utilization of a transmit angle reference memory 528 allows for the enabling of sonic transmission and echo reception between transducer and patient in accordance with parameters established by the user via reference 528.

Each time the angle comparator 529 denotes identity between the present mirror angle from the servo control 507, and a reference angle from 528, the timing and control generator 508 is notified to energize a transmit-receive sequence as described previously. It is noted that utilization of the scan head in simple B-scan mode will be promoted by utilization of a single, unvarying reference angle from memory 528.

The reference angle from memory 528, together with actual positional information from the encoder, is processed at converter 530 to yield an x-y positional version of the angular information represented by the actual position of the mirror. This information in suitable digital form is coupled to a buffer or gate 531, which under the control of the function selection controls 519, is coupled to accumulators 532 and in turn to the digital image memory 515.

In summary, it will be seen that the principles of the present invention advantageously utilize well-known precepts relating to real time sector scanning and to static B-scan imaging, and combine the two to yield substantially advantageous operation. Preferred and illustrative embodiments of the principles of the present invention have been presented. It will be understood, however, that those of ordinary skill in the art will devise numerous alternative embodiments which nevertheless fall within the spirit or the scope of the principles of the present invention.

I claim:

1. An ultrasound imaging system comprising:
   (a) an articulated scan arm having an outermost terminus adapted to carry a transducer means, said scan arm including means for generating positional information concerning said outermost terminus based on the relative positions of segments of said scan arm;
   (b) transducer means, removably attached to said outermost terminus of said scan arm; and
   (c) means for selectively operating said transducer means to produce a sector of beams or to generate sonic beams only along a given axis.

2. A system as described in claim 1 wherein said transducer means comprises a detachable, independently operable real time sector scan probe.

3. A system as described in claim 2 wherein said outermost terminus comprises bracket means for carrying said probe such that said given axis is in direct alignment with said outermost terminus.

4. A system as described in claim 1 and further including image processing and display means, responsive to positional information from said scan arm and from said means for operating, for assembling an image based on sonic energy transmissions from said transducer means, and sonic echoes received by said transducer means.

5. A system as described in claim 4 wherein said display means includes means for processing a real time sector image.

6. A system as described in claim 1 wherein said transducer means includes:
   (a) a positionally fixed transducer;
   (b) a sonic reflector facing said transducer and inclined to deflect sonic energy between said transducer and a patient; and
   (c) means for oscillating said mirror on an axis, thereby correspondingly to oscillate the direction of said deflection.

7. A system as described in claim 6 wherein said means for operating comprises means for selectively maintaining said reflector in a fixed predetermined position with respect to said axis.

8. A system as described in claim 1 wherein said transducer means comprises a plurality of transducer elements arrayed with respect to one another in a predetermined spatial orientation.

9. A system as described in claim 8 wherein said transducer elements comprise an annular array.

10. A system as described in claim 8 wherein said transducer elements comprise a linear array.

11. In an ultrasound imaging system having a real time sector scan probe independently operable but freely attachable to and detachable from the terminus of an articulated scan arm, said probe comprising transducer means and means for selectively operating said transducer means to produce a sector of beams or to generate sonic beams only along a given axis, said scan arm producing information denoting the location of a transducer located at said terminus, a method of conducting ultrasound examinations comprising:
 (a) detaching said probe from said arm and conducting a free hand real time scan of an area in interest;
 (b) attaching said probe to said arm and repeating salient portions of said real time scan, while recording positional information for particular conditions in interest;
 (c) shifting the scan mode of said probe, while attached to said arm, from real time to static B-scan operation by adjusting said means for selectively operating said transducer means to generate sonic beams only along a given axis; and
 (d) performing static B-scan investigations of said conditions in interest based on said recorded positional information.

12. A method as described in claim 11 and further comprising the steps of generating a hard copy record during said repeated real time scan and during said static B-scan.

* * * * *